(12) United States Patent
Dees et al.

(10) Patent No.: US 10,722,249 B2
(45) Date of Patent: *Jul. 28, 2020

(54) SYSTEM FOR ORTHOPEDIC IMPLANTATION PREPARATION

(71) Applicant: Smith & Nephew, Inc., Memphis, TN (US)

(72) Inventors: Roger Ryan Dees, Senatobia, MS (US); Jeffrey N. Yeager, Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 284 days.

This patent is subject to a terminal disclaimer.

(21) Appl. No.: 15/572,967

(22) PCT Filed: May 13, 2016

(86) PCT No.: PCT/US2016/032399
§ 371 (c)(1),
(2) Date: Nov. 9, 2017

(87) PCT Pub. No.: WO2016/183459
PCT Pub. Date: Nov. 17, 2016

(65) Prior Publication Data
US 2018/0344333 A1    Dec. 6, 2018

Related U.S. Application Data

(60) Provisional application No. 62/161,031, filed on May 13, 2015.

(51) Int. Cl.
*A61B 17/17* (2006.01)
*A61B 17/16* (2006.01)
(Continued)

(52) U.S. Cl.
CPC ........ *A61B 17/1764* (2013.01); *A61B 17/164* (2013.01); *A61B 17/1659* (2013.01);
(Continued)

(58) Field of Classification Search
CPC ............ A61B 17/1717; A61B 17/1764; A61B 17/1675
See application file for complete search history.

(56) References Cited

U.S. PATENT DOCUMENTS 4,791,919 A    12/1988  Elloy et al.
8,187,280 B2    5/2012  May et al.
(Continued)

FOREIGN PATENT DOCUMENTS

CN    101835441 A    9/2010
EP    0194014 B1    9/1986
(Continued)

OTHER PUBLICATIONS

International Search Report; European Patent Office; International Application No. PCT/US2016/032399; dated Mar. 13, 2017; 8 pages.
(Continued)

*Primary Examiner* — Andrew Yang

(57) ABSTRACT

A system for preparing a bone for implantation of a component of an orthopedic implant device. The system includes a forming tool having a sleeve member that is selectively received within a handle member. The sleeve member has a guide slot that is sized to receive axial passage of at least a portion of a guide. The guide slot and/or sleeve member may be positioned and/or configured to facilitate at least linear and/or rotational displacement of the forming tool about, or relative to, the guide, and thereby provide a degree of freedom in the location at which the forming tool may form a shape or opening in the bone relative to one or more
(Continued)

reference axes. The handle member may include a connection member that is structured to be operably coupled to a bone preparation device that is structured to facilitate the displacement of bone material.

18 Claims, 13 Drawing Sheets

(51) Int. Cl.
*A61F 2/46* (2006.01)
*A61B 90/00* (2016.01)

(52) U.S. Cl.
CPC .......... *A61B 17/1675* (2013.01); *A61B 17/17* (2013.01); *A61B 17/1717* (2013.01); *A61F 2/461* (2013.01); *A61B 2090/0811* (2016.02); *A61F 2/4603* (2013.01)

(56) References Cited

U.S. PATENT DOCUMENTS

| | | | |
|---|---|---|---|
| 9,095,356 | B2 | 8/2015 | Thomas et al. |
| 9,386,999 | B2 | 7/2016 | Robertson et al. |
| 2005/0075640 | A1* | 4/2005 | Collazo .............. A61B 17/1675 606/86 R |
| 2013/0012941 | A1 | 1/2013 | Dees et al. |
| 2013/0317501 | A1 | 11/2013 | Booth et al. |
| 2013/0325136 | A1 | 12/2013 | Thomas et al. |
| 2014/0276858 | A1 | 9/2014 | Major et al. |

FOREIGN PATENT DOCUMENTS

| | | |
|---|---|---|
| JP | S61-209654 A | 9/1986 |
| JP | 2013-248398 A | 12/2013 |
| JP | 2014-176669 A | 9/2014 |

OTHER PUBLICATIONS

Written Opinion of the International Searching Authority; European Patent Office; International Application No. PCT/US2016/032399; dated Mar. 13, 2017; 8 pages.

Examination report No. 1 for Australian Patent Application No. 2016260438, dated Jan. 28, 2020.

Notice of Reasons for Rejection for Japanese Patent Application No. 2017-557170, dated Jan. 20, 2020.

First Office Action for Chinese Patent Application No. 201680027699.8, dated Dec. 30, 2019.

* cited by examiner

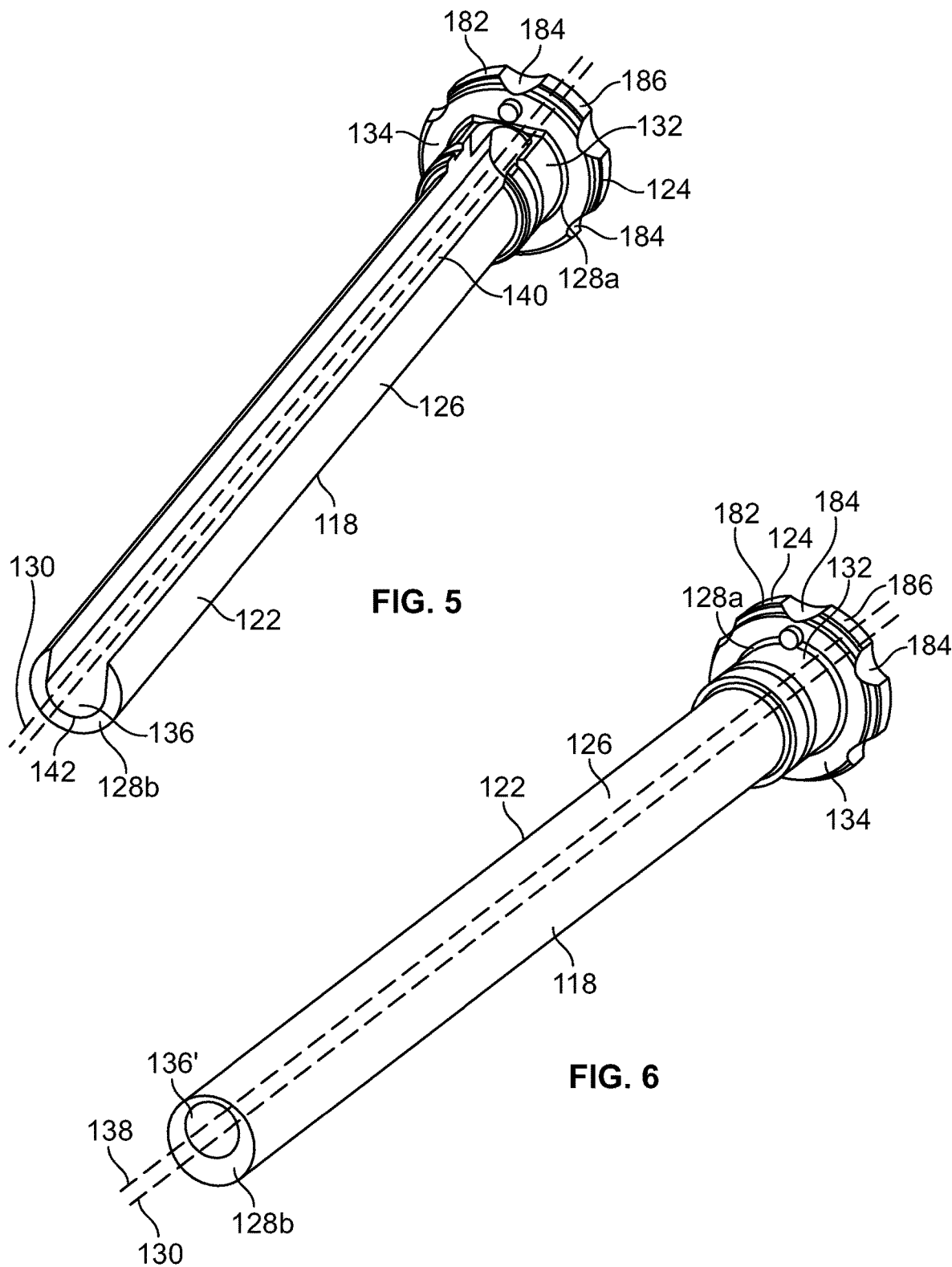

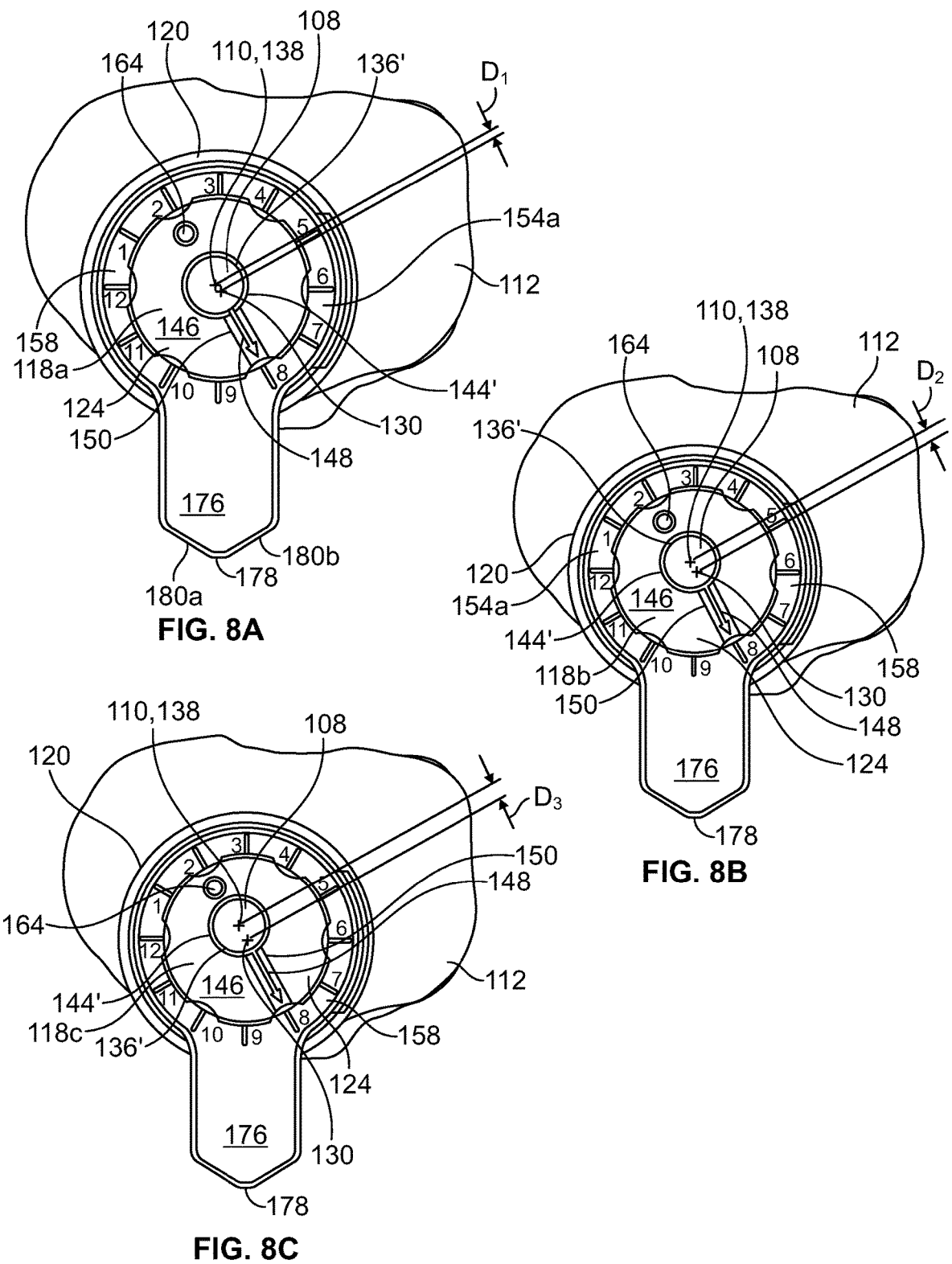

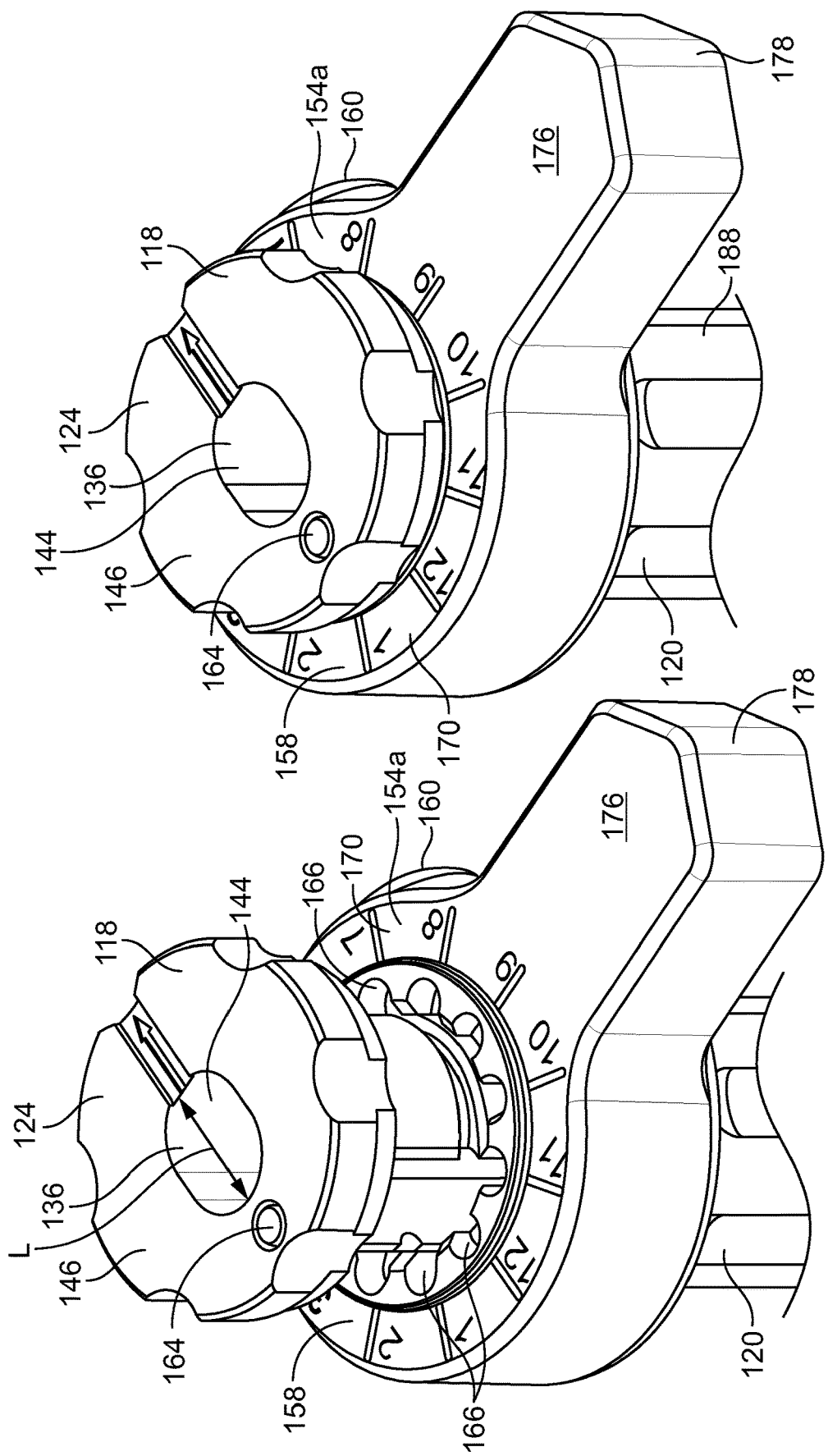

SYSTEM FOR ORTHOPEDIC IMPLANTATION PREPARATION

CROSS-REFERENCE TO RELATED APPLICATIONS

The present application is a U.S. National Phase of International PCT Application No. PCT/US2016/032399 filed May 13, 2016, which claims the benefit of U.S. Provisional Application Ser. No. 62/161,031 filed May 13, 2015, the contents of each application are incorporated herein by reference in their entirety.

BACKGROUND

Embodiments of the present application generally relate to preparatory instrumentation for implantation of an orthopedic implant or component in a bone. More particularly, but not exclusively, embodiments of the present application relate to instrumentation for implantation of a metaphyseal and/or diaphyseal implant or augment relative to, and with selectively limited freedom about, one or more reference axis(es).

Proper alignment of a replacement joint device, including components of the replacement joint device, often can contribute to attaining optimal wear resistance performance of the implanted device. Yet, anatomical variations present challenges in properly aligning the implant device for each patient. For example, during implant construct of knee replacement joints, challenges can arise with fitting a patient's intramedullary geometry with an implant, such as, for example, an intramedullary stem, while also fitting both the external geometry with a condylar replacing implant and the metaphyseal and/or diaphyseal geometry with an associated implant or augment component. Moreover, the addition of a metaphyseal and/or diaphyseal implant or augment to an implant construct often impairs the ability to adjustably fit the implant to the patient and/or attain proper alignment of the various components of the implant. Such difficulties can at times be attributed to the anatomy of the patient, the geometrical constraints of the implant, and/or constraints associated with the preparatory instrumentation. For example, geometrical constraints of the metaphyseal and/or diaphyseal implant or augment can include the inability to accommodate the placement or position of both the intramedullary stem and the condylar implant, which can attribute to difficulties in forming a junction mechanism for those, and possibly other, components of the implant.

Challenges associated with attaining proper alignment during implant construct that involves a metaphyseal and/or diaphyseal implant or augment may have, at times, been resolved by compromises in terms of the placement of at least some components of the implant device, such as, for example, the location of the condylar implant. Yet, such compromises can result in less than optimal bone coverage, which can potentially compromise loading of the construct to the cortical rim of the bone. Other compromises can include reducing the stem size in order to offset the stem position, with the area vacated by such offsetting being made up with cement. Yet, such compromises can adversely impact the life of the implant, and can be, at least in part, attributable to failures relating to subsidence, loosening, stress-shielding factors, and increased stresses on the implant device, among other failures that are associated with compromised articulation positioning.

The integrity of the implant construct can therefore be adversely impacted if the bone is not shaped, during implant surgery, to accommodate the positioning of augmenting implants at locations in which the implanted augments, such as, for example, stems, sleeves, and cones, among other augments, will not interfere with the articular component and/or other augmenting implants. Yet, the different anatomies of patients often present challenges in the ability to position augmenting implants at optimal locations. For example, in order to achieve optimal bone coverage, the articular component stem connection (post) axis can need to be at a location that is different than the stem axis. Further, the inability to attain such positioning can lead to compromises in the structure, life span, and/or performance of the implanted device, among other compromises.

BRIEF SUMMARY

An aspect of the present application is an apparatus for use with a bone preparation device, the apparatus having a sleeve member that has a guide slot that is sized to receive axial passage of at least a portion of a guide. The guide slot is sized so accommodate linear displacement of the sleeve member about the received guide in one or more directions that are perpendicular to a longitudinal guide axis of the guide. The apparatus also includes a handle member that has an inner area that is sized to receive insertion of at least a portion of the sleeve member, the handle member having a connection member structured to be coupled to the bone preparation device. The apparatus further includes a retention member that is adapted to selectively secure the sleeve member to the handle member at a selected one of a plurality of rotational positions, each of the plurality of rotational positions adjusting an angular position of at least the sleeve member relative to the handle member.

Another aspect of the present application is an apparatus for use with a bone preparation device, the apparatus including a sleeve member that has a guide slot that is sized to receive axial passage of at least a portion of a guide. Additionally, the guide slot has a central guide slot axis that is offset from a longitudinal sleeve axis of the sleeve member. The apparatus also includes a handle member that has an inner area that is sized to receive removable insertion of at least a portion of the sleeve member. The handle member also has a connection member that is structured to be coupled to the bone preparation device. The apparatus further includes a retention member that is adapted to selectively secure the sleeve member to the handle member at a selected one of a plurality of rotational positions, each of the plurality of rotational positions adjusting an angular position of at least the guide slot relative to a longitudinal handle axis of the handle member.

Another aspect of the present application is a bone preparation device that has a sidewall that extends about a central cutting axis of the bone preparation device. The sidewall has an outer surface an inner surface, the outer surface being structured to facilitate displacement of bone material, and the inner surface defining an aperture in the bone preparation device. The bone preparation device also includes an upper wall that is adjoined to the sidewall. The upper wall has an opening that is in fluid communication with the aperture. The opening includes a pair of opposing recesses that are structured to extend a portion of a size of a portion of the opening. The opening further includes a slot that outwardly extends from one of the pair of opposing recesses. Additionally, the upper wall defines, in part, a cavity that is adjacent to an inner wall of the upper wall. The cavity is structured to extend a size of a portion of the aperture.

BRIEF DESCRIPTION OF THE DRAWINGS

The description herein makes reference to the accompanying figures wherein like reference numerals refer to like parts throughout the several views.

FIG. 5 illustrates a side perspective view of a sleeve member for a forming tool having as elongated guide slot according to an illustrated embodiment of the present application.

FIG. 6 illustrates a side perspective view of a sleeve member for a forming tool having an offset guide slot according to an illustrated embodiment of the present application.

FIGS. 8A-C illustrate examples of top views of a forming tool in which a guide is positioned within guide slots having various linear offset distances and in which the sleeve member is positioned relative to a handle member to adjust an angular position of at least the forming tool relative to the guide.

FIG. 9 illustrates a top perspective view of a portion of a forming tool in which a sleeve member having an elongated guide slot is being positioned relative to a handle member of the forming tool according to an illustrated embodiment of the present application.

FIG. 10 illustrates a top perspective view of a portion of a forming tool in which a sleeve member having an elongated guide slot is secured to a handle member according to an illustrated embodiment of the present application.

Figure 1:
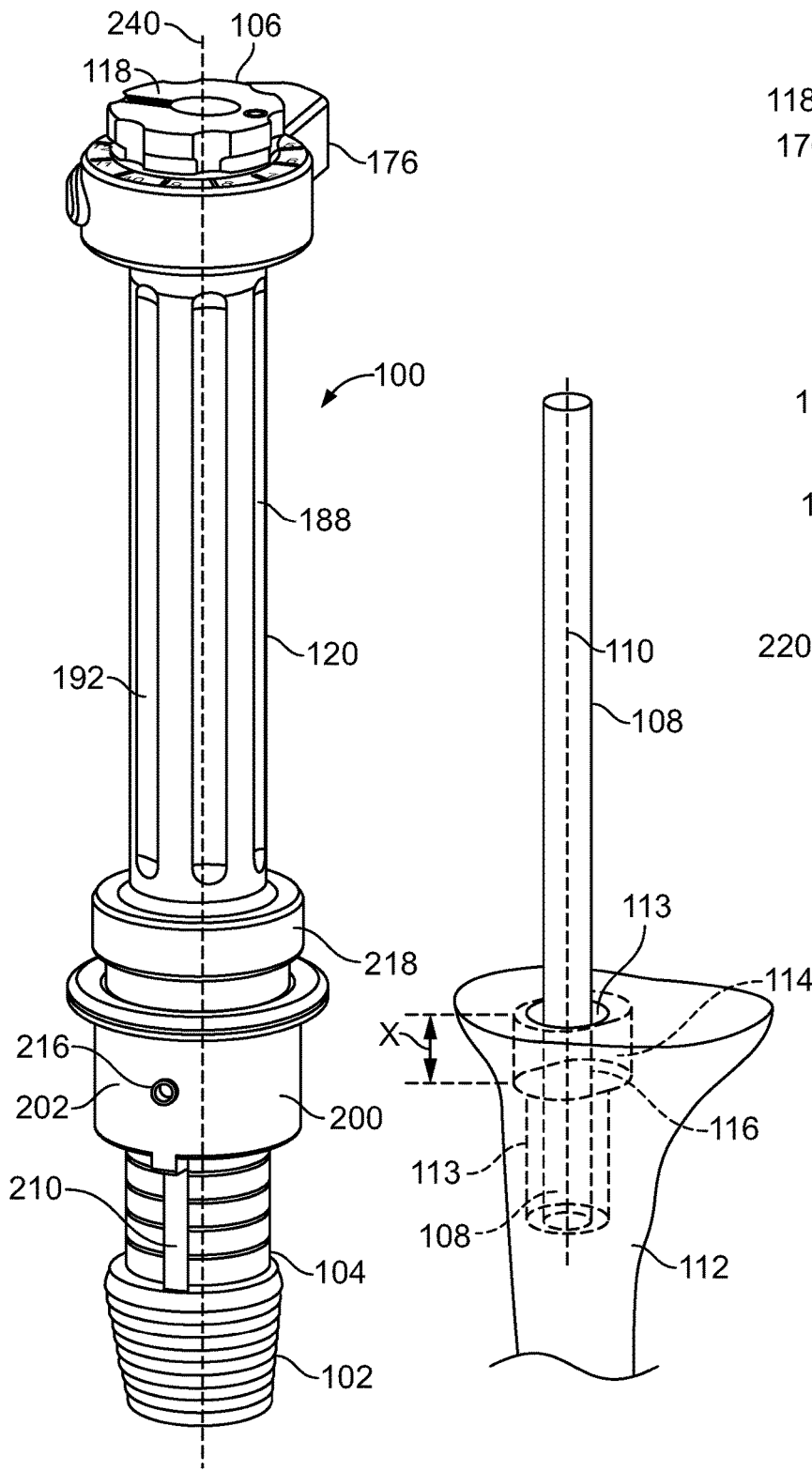
FIG. 1 illustrates a front perspective view of a forming tool for preparing a bone for implantation of an augment or implant device according to an illustrated embodiment of the present application.

The foregoing summary, as well as the following detailed description of certain embodiments of the present application, will be better understood when read in conjunction with the appended drawings in which like reference numbers indicate like features, components and method steps. For the purpose of illustrating the invention, there is shown in the drawings, certain embodiments. It should be understood, however, that the present invention is not limited to the arrangements and instrumentalities shown in the attached drawings.

DESCRIPTION OF THE ILLUSTRATED EMBODIMENTS

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 2:
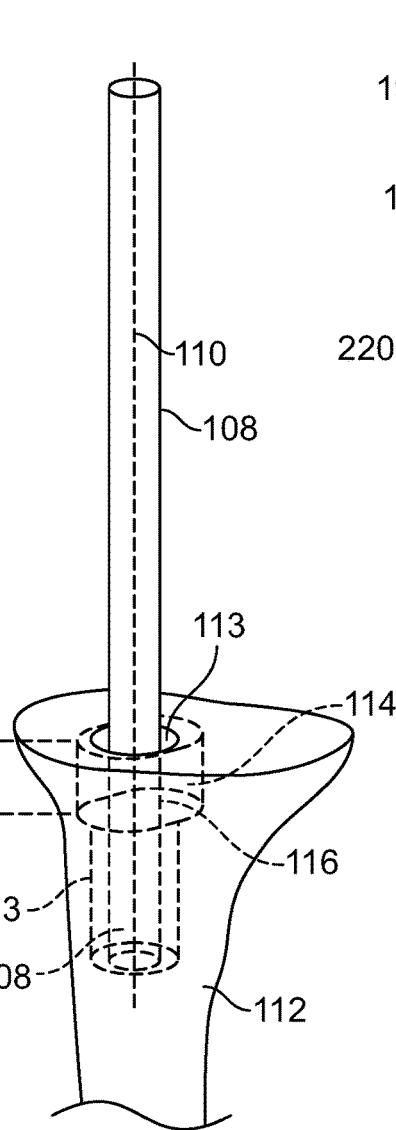
FIG. 2 illustrates a front perspective view of an orientation referencing instrument or guide that extends along a longitudinal guide axis and which is inserted into an intramedullary canal of a patient.
Figure 3:
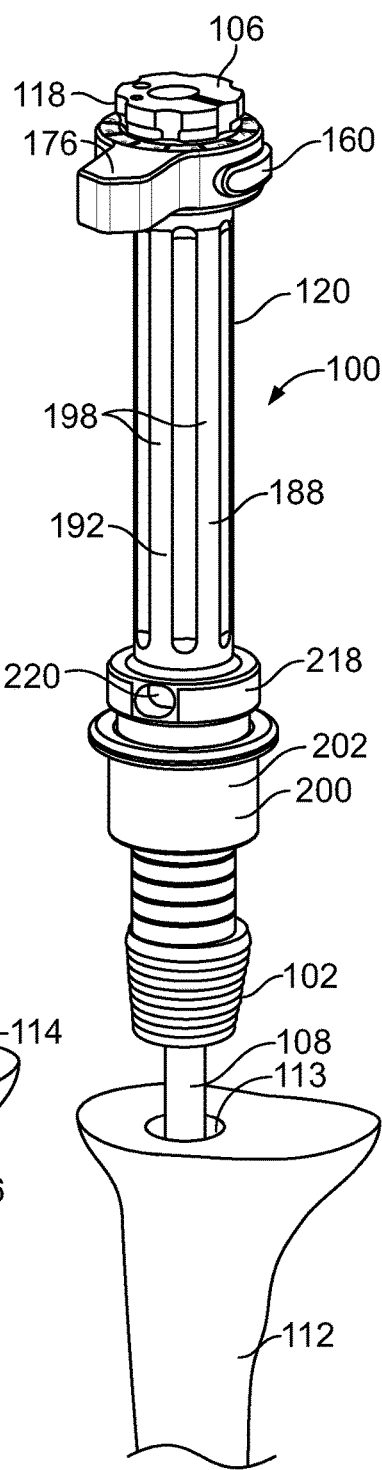
FIG. 3 illustrates a front perspective view of at least a portion of the guide shown in FIG. 2 being positioned within at least a portion of the forming tool depicted in FIG. 1.

FIG. 1 illustrates a front perspective view of a forming tool 100 for preparing a bone for implantation of an augment or other implant component (collectively referred to as "augment") according to an illustrated embodiment of the present application. The forming tool 100 includes a bone preparation device 102 that is selectively coupled to a distal end 104 of the forming tool 100, as discussed below. As also discussed below in more detail, a proximal end 106 of the forming tool 100 is adapted to at least assist in selectively adjusting the location for forming a cut in a bone using the bone preparation device 102 at either, or both, a distance and direction away from one or more reference axis(es). The forming tool 100 is structured to receive insertion of, or otherwise engage, at least a portion of an orientation referencing instrument or guide 108, such as, for example, a intramedullary rod, trial stem, reamer, or offset rod, among other guides, as shown in FIGS. 2 and 3. According to the example provided in FIGS. 2 and 3, the guide 108 is an intramedullary rod that extends along a longitudinal guide axis 110, which may, or may not, be aligned with a longitudinal reference axis of the intermedullary canal 113 in the patient's bone 112. Further, according to the illustrated embodiment, the bone preparation device 102 is adapted to form an augment opening 114 having a depth (as indicated by "X" in FIG. 2) in the bone 12. Further, the augment opening 114 is positioned about a central augment axis 116, as shown for example, in FIG. 2, and can be generally at the same location, or can be angularly and/or linearly offset from one or more axes, a reference axis, such as, for example, the longitudinal guide axis 110.

As shown by at least FIGS. 1 and 3-5, according to the illustrated embodiment, the forming tool 100 includes a sleeve member 118 and a handle member 120. The sleeve member 118 includes a guide body 122 and a selector body 124. An outer wall 126 of the guide body 122 extends between opposing first and second ends 128a, 128b of the guide body 122, the first end 128a being adjacent to the selector body 124. The outer wall 126 of the guide body 122 can have a variety of shapes and sizes. For example, in the illustrated embodiment, at least a portion of the outer wall 126 has a generally elongated cylindrical shape that extends along a longitudinal sleeve axis 130 of the sleeve member 118. The outer wall 126 can also form a hub portion 132 of the guide body 122 that extends from a lower portion 134 of the selector body 124.

The guide body 122 includes a guide slot 136 that extends along at least a portion of the outer wall 126, and which is sized to receive the insertion of at least a portion of the guide 108. During operation of the forming tool 100 and/or the bone preparation device 102, the guide 108 can be secured to the forming tool 100, such as, for example, via use of a retaining mechanism, including, but not limited to, a threaded, slotted, or spring capture retaining mechanism, among others.

The guide slot 136 can have a variety of different shapes and sizes. For example, as depicted in at least FIGS. 6 and 8A-8C, according to certain embodiments, the guide slot 136' can have a generally cylindrical shape. However, according to other embodiments, the guide slot 136 can have an elongated shape, as shown, for example, in at least FIGS. 5 and 7A-7C. Additionally, according to certain embodiments, the guide slot 136, 136' can extend along a centrally located guide slot axis 138 that is generally the same as, or aligned with, the longitudinal sleeve axis 130 of the sleeve member 118. However, according to other embodiments, the guide slot axis 138 can be at least linearly offset, by varying distances, from the longitudinal sleeve axis 130 of the sleeve member 118, the longitudinal guide axis 110, and/or another reference axis(es). For example, according to the embodiments illustrated in FIGS. 8A-8C, the sleeve members 118a, 118b, 118c can be configured to provide guide slots 136' that each have different linear offset distances between the longitudinal sleeve 103 and the guide axis 110 and/or the guide axis slot 138, as indicated by offset distances $D_1$, $D_2$, and $D_3$, respectively. In the illustrated examples, linear offset distance $D_1$ is less than that of linear offset distance $D_2$, which is less than linear offset distance $D_3$. Thus, according to certain embodiments, the forming tool 100 can be modular in that sleeve members 118 having guide slots 136, 136' of different shapes, sizes, and/or positioning of the guide slot axis 138 relative to the longitudinal sleeve axis 130, among other reference axes, can be interchangeably selected for operable engagement with the handle member 120, and thus for use with the forming tool 100.

Referencing FIG. 5, according to certain embodiments, the guide slot 136 can extend through a portion of the outer wall 126 so as to provide the guide slot 136 with a depth that extends from an opening 140 of the guide slot 136 to a bottom portion 142 of the guide slot 136. According to such an embodiment, the bottom portion 142 of the guide slot 136 can correspond to a portion of the outer wall 126, with the bottom portion 142 and the opening 140 of the guide slot 136 being generally at opposing sides or ends of the guide slot 136. Further, according to such embodiments, the depth of the guide slot 136 can allow for adjustments in the location of at least the guide 108 within the guide slot 136, and thereby permit adjustments of the location of at least the guide 108 relative to the guide slot axis 138 and/or the longitudinal sleeve axis 130. Further, according to certain embodiments, one or more sleeve members 118 can have guide slots 136 of different depths, thereby allowing for the selection of a guide body 122 that may, or may not, offset the guide 108 from at least the guide slot axis 138 by a predetermined or maximum distance.

Referencing FIGS. 7A-12, the selector body 124 of the sleeve member 118 can include an aperture 144, 144' that is in fluid communication with the guide slot 136, 136'. According to certain embodiments, the aperture 144, 144' can have a shape that is generally similar to the shape, or is an extension, of the guide slot 136, 136', such as, for example, having a generally circular or elongated shape. However, the aperture 144, 144' of the selector body 124 can have a variety of other shapes. For example, according to the illustrated embodiment, the aperture 144, 144' can have a generally elongated shape, such as, for example, have a linear length (as indicated by "L" in FIG. 9) that is generally aligned with or exceeds the size or depth of the guide slot 136, 136' so as to facilitate visual detection through the aperture. 144, 144' and/or the position or location of the guide 108 in the guide slot 136, 136'.

An upper surface 146 of the selector body 124 can also include an indicator 148 that facilitates a determination of an angular orientation of at least the guide slot 136, 136', guide slot axis 138, and/or the guide 108 relative to a reference axis, as discussed below. In the illustrated embodiment, the indicator 148 can include an indicium, such as, for example, a word or symbol, including, but not limited to, an arrow. Further, according to certain embodiments, the indicium can be positioned on an upper surface 146 of the selector body 124, such as, for example, in a groove 150 within the upper surface 146.

Figure 13:
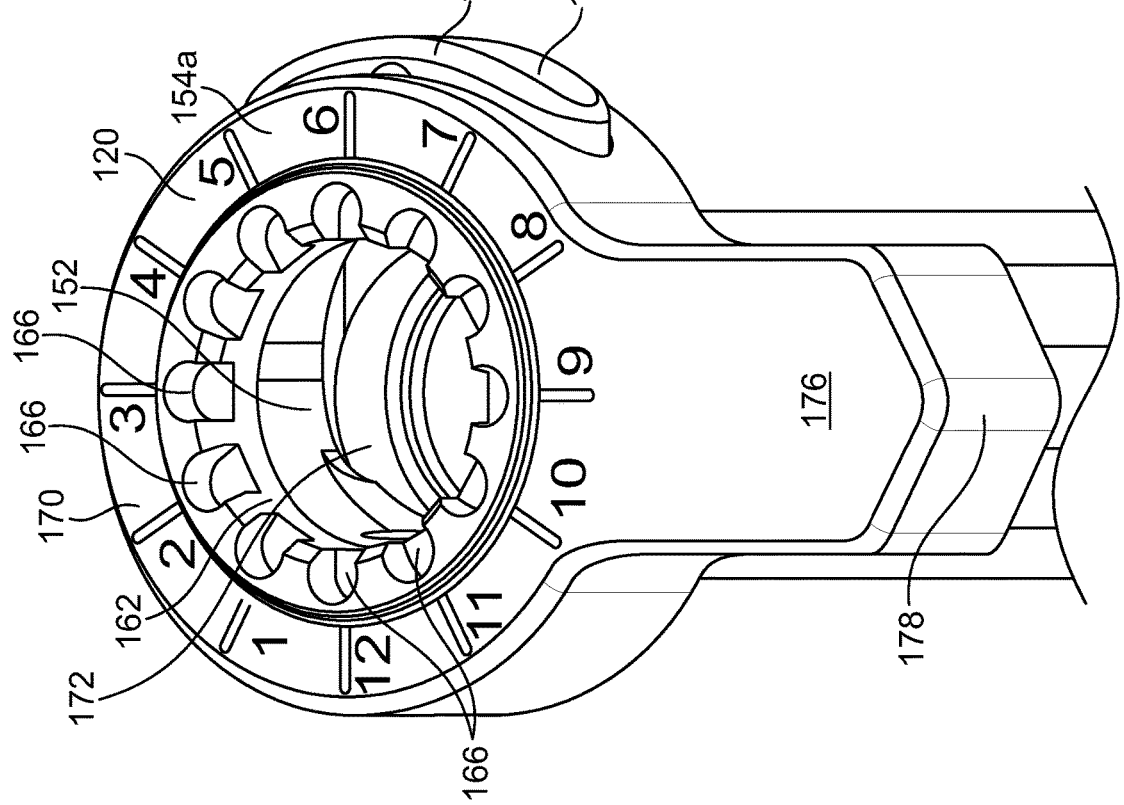
FIG. 13 illustrates a top perspective view of a portion of a handle member of a forming tool according to an illustrated embodiment of the present application.

As shown by at least FIG. 13, the handle member 120 has an inner area 152 that extends through the handle member 120, at least a portion of the inner area 152 being sized to receive insertion of at least the guide body 122 of the sleeve member 118. Further, a first end 154a of the handle member 120 can be adapted for selective locking engagement with the sleeve member 118. For example, according to the illustrated embodiment, the sleeve member 118 and the handle member 120 can be adapted for selectively releasable locking engagement that prevents both axial and rotational displacement of the sleeve member 118 relative to the handle member 120. For example, the forming tool 100 can include a lock member 156 that is adapted to retain the sleeve member 118 within the inner area 152 of the handle member 120 in a manner that can prevent axial displacement of the sleeve member 118 relative to the handle member 120, while the selector body 124 of the sleeve member 118 is adapted for locking engagement with a selector hub 158 of the handle member 120.

According to certain embodiments, the lock member 156 can be adapted to be displaceable between a first, locked position and a second, unlocked position. For example, according to certain embodiments, at least a portion of the lock member 156 can extend into at least the inner area 152 of the handle member 120 when the lock member 156 is in the first, locked position. According to certain embodiments, when the guide body 122 is inserted into the inner area 152 of the handle member 120, the guide body 122 can engage the lock member 156 in a manner that displaces the lock member 156 from the first, locked position and to, and/or toward, the second, unlocked position. According to such embodiment, as the lock member 156 is displaced to and/or toward, the second, unlocked position, at least a portion of the lock member 156 can be withdrawn from, or otherwise displaced within, the inner area 152. According to other embodiments, when the guide body 122 is to be inserted into the inner area 152, the user can exert a force against an outer selector or button 160 of the lock member 156 that displaces at least a portion of the lock member 156 in and/or from the inner area 152 so that the lock member 156 does not prevent insertion of the guide body 122 into the inner area 152. Further, with the guide body 122 positioned in the inner area 152, the lock member 156 can be displaced toward, or to, the first, locked position so that the lock member 156 is positioned to engaged the guide body 122 in a manner that prevents the axial displacement of the sleeve member 118 relative to the handle member 120. For example, a portion of lock member 156 can be received in a groove or recess in, or above a portion of, the hub portion 132 of the guide body 122 so as to prevent the axial displacement of the sleeve member 118 relative to the handle member 120. According to such embodiments, when the guide body 122 is to be withdrawn from the inner area 152 of the handle member 120, the user can exert a force against the outer selector or button 160 of the lock member 156 that displaces at least a portion of the lock member 156 toward or to the second, unlocked position, so that the lock member 156 is at a position that does not prevent the removal of the guide body 122 from the inner area 152.

The handle member 120 can also be structured for selective, locking engagement with a portion of the sleeve member 118 so as to secure at least the angular position of the sleeve member 118 relative to the handle member 120. For example, according to certain embodiments, a portion of the outer wall 126 of the sleeve member 118 and an inner wall 162 of the handle member 120 can include portions of a retention member 164 that can compromise, for example, one or more mating splines, keys, or teeth that facilitate selective, locking engagement in a manner that permits the positioning, and, if necessary, re-positioning of the rotational position of the sleeve member 118 relative to the handle member 120. According to certain embodiments, such mating splines can be positioned at, or around, the selector hub 158 portion of the handle member 120 and the selector body 124 of the guide body 122.

Figure 14:
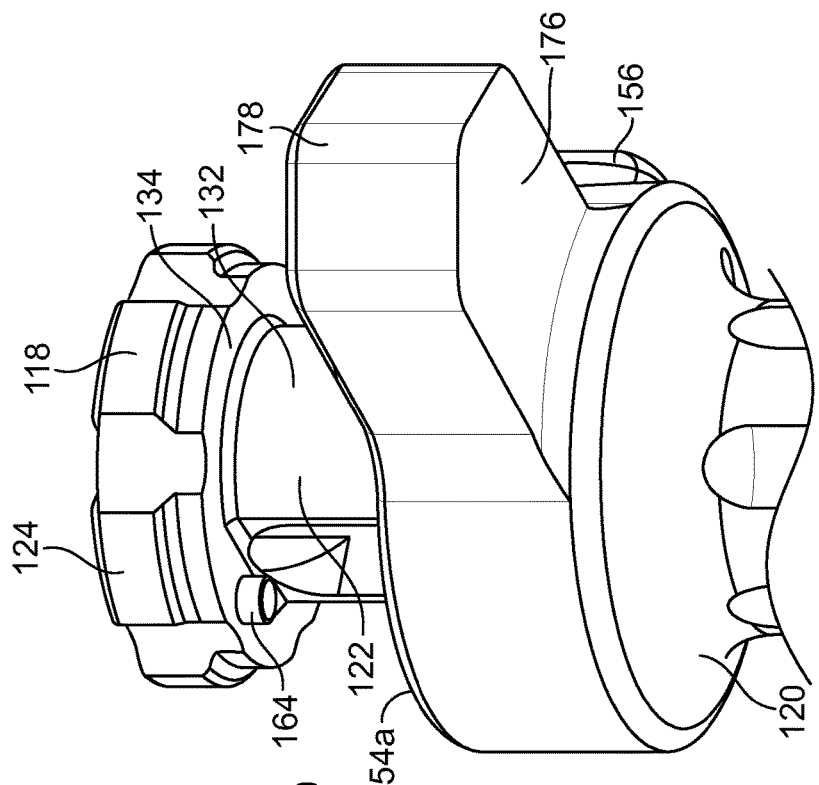
FIG. 14 illustrates a bottom perspective view of a sleeve member being inserted into a guide member according to an illustrated embodiment of the present application.

As illustrated in FIG. 14, according to other embodiments, the retention member 164 can be a pin that at least projects or extends at least from the lower portion 134 of the selector body 124 and is received in one or more retention openings 166 along the handle member 120. A variety of different types of pins can be utilized for the projection member 164, including, for example, a separate pin(s) that can be secured to the selector body 124 by a press fit, adhesive, or plastic weld, among other manners of attachment. Alternatively, the pin(s) can be a unitary, monolithic portion or extension of the selector body 124. Further, the pin(s) can have a variety of different shapes and sizes, including having a generally circular or non-circular cross-sectional shape. Further, the shape and/or size of such a pin can be uniform or non-uniform as the pin extends away from the selector body 124. Additionally, according to certain embodiments, at least a portion of the retention member 164 can be exposed or otherwise visible from or through the upper surface 146 of the selector body 124. For example, according to certain embodiments, the retention member 164 can be positioned in an aperture 168 that extends through the selector body 124, thereby exposing at least an end of the retention member 164 at the upper surface 146 of the selector body 124. Such visual access to the retention member 164 from the upper surface 146 of the selector body 124 can allow the retention member 164 to also provide another indication of the angular orientation of the guide slot 136, 136' relative to the handle member 120. Additionally, a visual indication of the angular location of the retention member 164 from the upper surface 146 of the selector body 124 can also facilitate positioning of the retention member 164 into locking engagement with a selected retention opening 166.

Referencing FIGS. 9-13, an upper wall 170 at the first end 154a of the handle member 120 can include indicium that corresponds to one or more of the retention openings 166. For example, in the illustrated embodiment, twelve retention openings 166 are positioned in a circular configuration about the upper wall 170 of the selector hub 158 and around, or adjacent to the opening 172 to the inner area 152. Further, rotational position indicators 174 can correspond to the location of the retention openings 166, which are identified in the depicted embodiment by a line and a corresponding number, namely, numbers "1" through number "12". However, a variety of other rotational positional indicators 174 can be employed. The rotational position indicators 174 can provide an indication of the rotational position of at least the guide slot 136, 136' and/or guide slot axis 138 relative to reference axis, such as, for example, the rotational position of the offset guide slot axis 138, and/or the longitudinal sleeve axis 130, among other reference axes.

The handle member 120 can also include a reference indicator 176 that can be structured for positioning and/or orientating at least the handle member 120 relative to a reference point, location, and/or direction, such as, for example, indicate a direction or orientation toward a particular portion of the bone 112 or another instrument, among other reference points. According to the illustrated embodiment, the reference indicator 176 can extend away from the selector hub 158 of the handle member 120. Further, an end 178 of the reference indicator 176 can be configured to improve the ease at which the reference indicator 176 is positioned and/or orientated, or otherwise directed toward the reference point, location, and/or direction. For example, according to the illustrated embodiment, the reference indicator 176 can include a pair of opposing, converging end walls 180a, 180b that are joined together to generally form a point so as to provide the reference indicator 176 with a pointed or arrow-shaped configuration. Moreover, the point at the end 178 can provide a generally centralized area that can improve the ease at reference can be made to the reference point, location, and/or direction when orienting the position or location of at least the handle member 120.

The selector body 124 can also be shaped or configured to facilitate the ability to grip or otherwise manipulate the position of the sleeve member 118, such as, for example, the angular position of the sleeve member 118 relative to the handle member 120. For example, according to the illustrated embodiment, an outer edge 182 of the selector body 124 can include a plurality or recesses 184 intermixed with a plurality of projections 186 that are structured to enhance the ability of a user to grasp, and/or retain a grasp of, the sleeve member 118. Such a configuration of the recesses 184 and projections 186 can also form a knurled surface along the outer edge 182.

Figure 4:
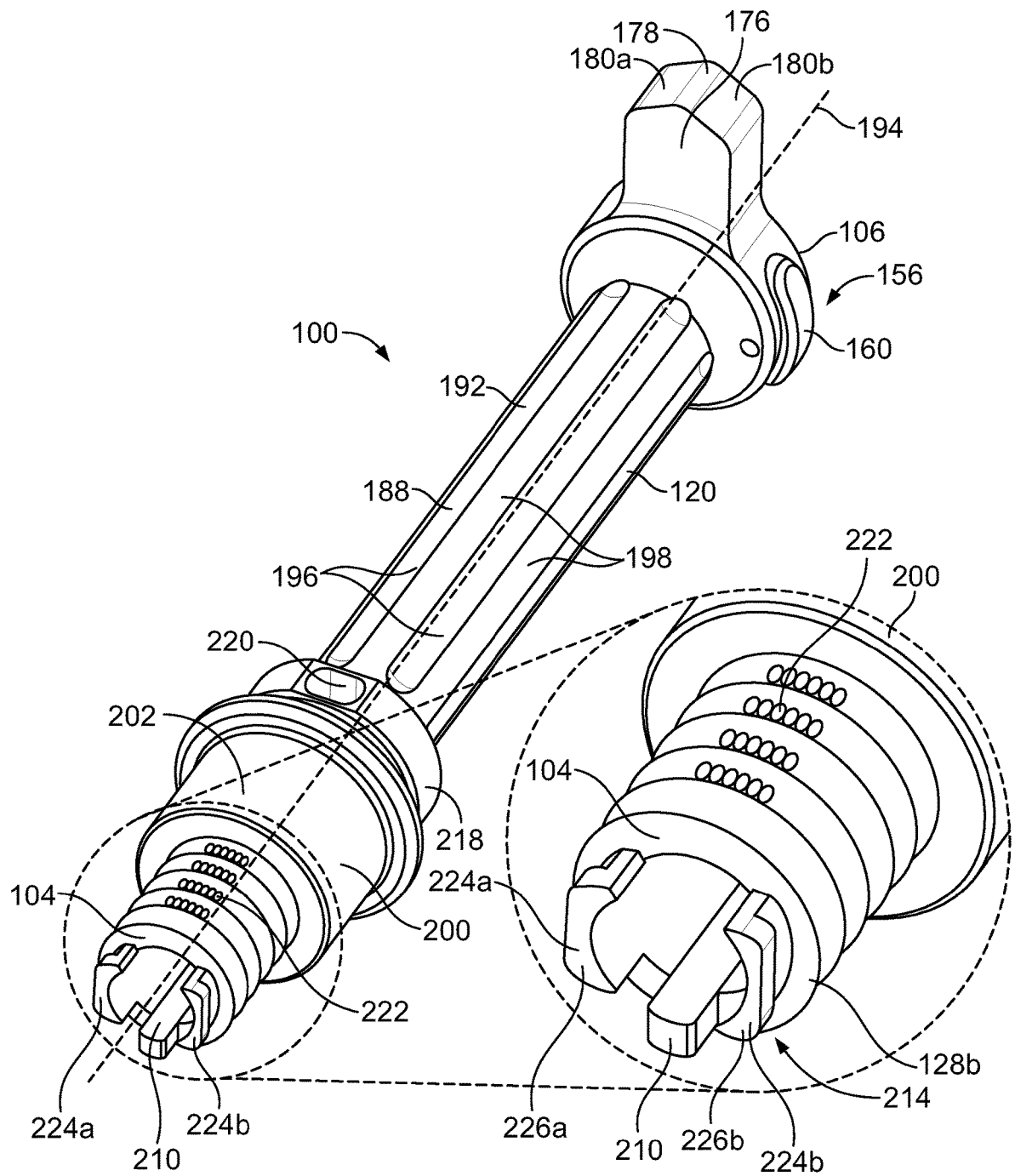
FIG. 4 illustrates a side perspective view of the forming tool shown is FIG. 1, without a bone preparation device, according to an illustrated embodiment of the present application.

A body portion 188 of the handle member 120 can extend between the selector hub 158 and a cutting assembly 190 of the handle member 120. According to the illustrated embodiment, the body portion 188 can include an outer wall 192 that has a generally cylindrical configuration that extends along a longitudinal handle axis 194, as shown in FIG. 4. When the sleeve member 118 is positioned within the inner area 152 of the handle member 120, the longitudinal handle axis 194 and the longitudinal sleeve axis 130 can at least be parallel and/or generally aligned together. Additionally, the outer wall 192 along the body portion 188 can include a plurality of intermixed recesses 196 that provide protrusions 198 therebetween, which can improve the ease with which a user can securely grip and/or grasp the body portion 188. Additionally, similar to other portions of the handle member 120, the inner area 152 can extend through the body portion 188. Further, according to the illustrated embedment, the inner area 152 along the body portion 188 can be sized to house at least a portion of the guide body 122 of the sleeve member 118.

The cutting assembly 190 can include an adjustable slide 200 that is adapted for axial displacement between first and second slide positions along a portion of the outer wall 192 of the handle member 120. According to the illustrated embodiment, the adjustable slide 200 can include an outer slide wall 202 and an inner slide wall 204, the inner slide wall 204 extending around at least a portion of the outer wall 192 of the handle member 120. The outer slide wall 202 can generally define an outer periphery of the adjustable slide 200. In the illustrated embodiment, the outer slide wall 202 extends along a hub portion 206 and a flange portion 208 of the adjustable slide 200. The adjustable slide 200 can also include, or be coupled to, an engagement member 210 that is configured to be received in a slot or groove 212 in the bone preparation device 102. According to certain embodiments, the engagement member 210 is a projection that extends from a lower surface or region of the adjustable slide 200 and extends to, or around, a region of a connection member 214 of the handle member 120, as discussed below. Further, the engagement member 210 and adjustable slide 200 can be part of a single, monolithic, or unitary construction. Alternatively, the engagement member 210 can be secured to the adjustable slide 200 by a fastener 216, such as, for example, by a pin or screw, among other fasteners.

Figure 15:
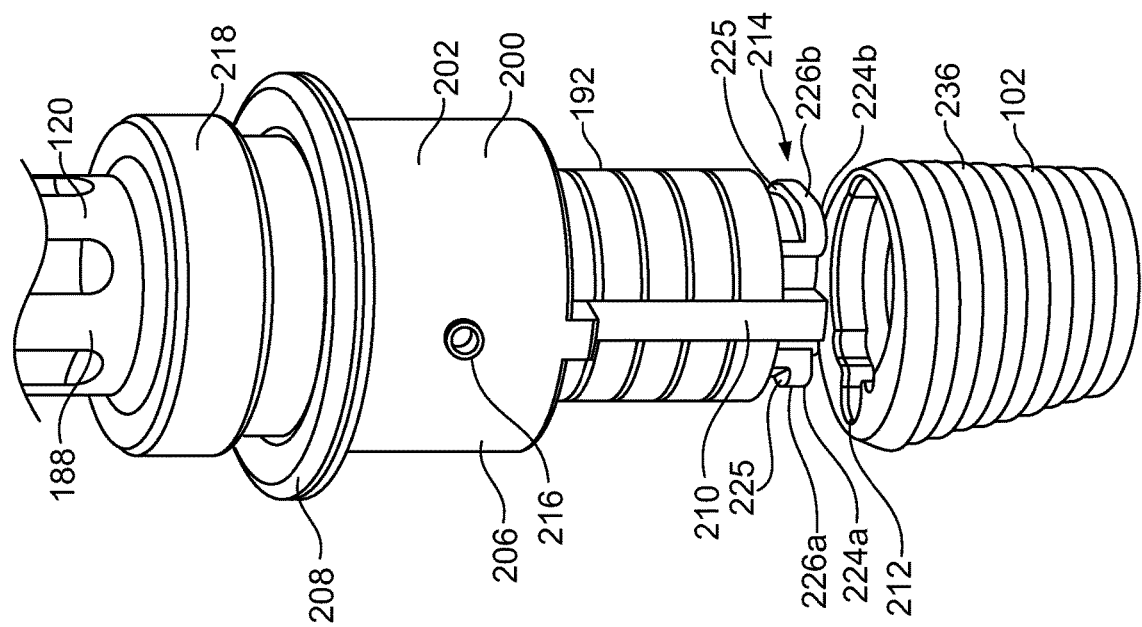
FIG. 15 illustrates a connection member of a forming tool with an adjustable slide in a first, lock position, and an example of a bone preparation device according to an illustrated embodiment of the present application.
Figure 17:
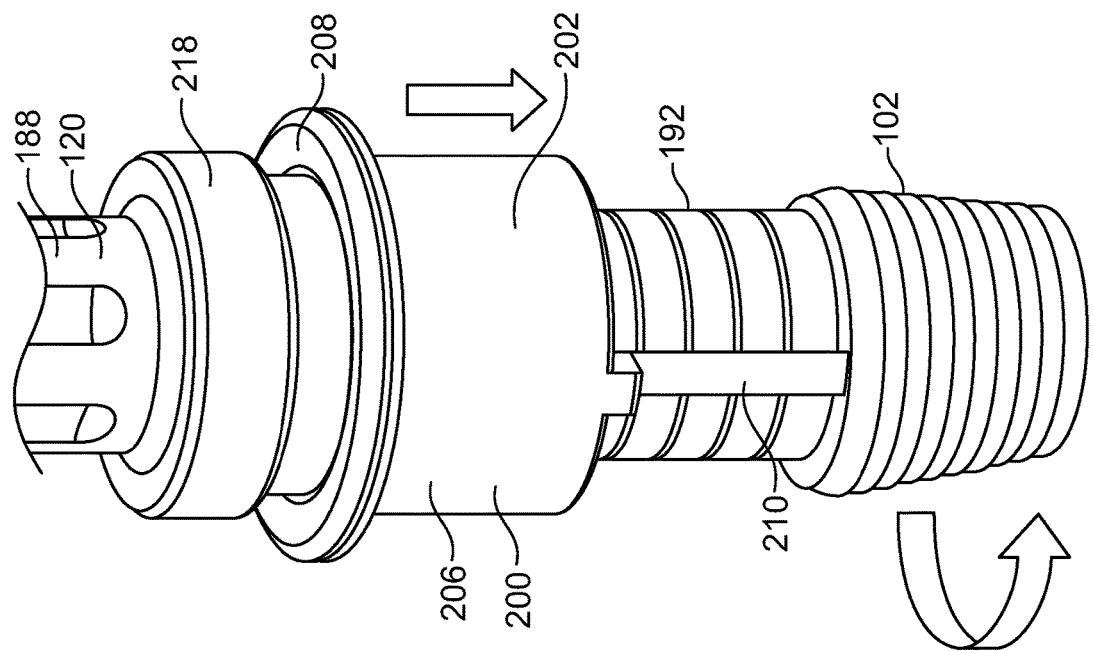
FIG. 17 illustrates a perspective view of the cutting assembly and the bone preparation device in FIG. 16 with the adjustable slide being axially displaced to the first, locked position and the forming tool being rotatably displaced relative to the bone preparation device to a locked position according to an illustrated embodiment of the present application.
Figure 16:
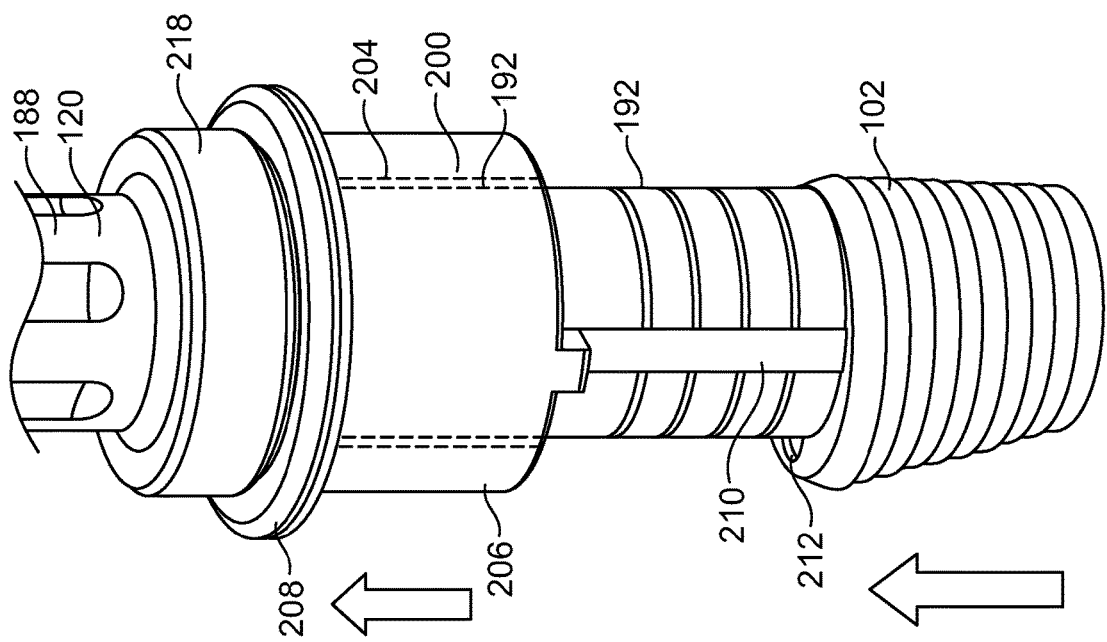
FIG. 16 illustrates an exemplary bone preparation device and an adjustable slide of a connection member being axially displaced to a second, unlocked position according to an illustrated embodiment of the present application.

According to certain embodiments, the adjustable slide 200 can be secured or biased in the first slide position, as illustrated for example in FIGS. 15 and 17. For example, according to certain embodiments, the cutting assembly 190 can include a biasing element, such as, for example, a spring, that biases the adjustable slide 200 to the first slide position. Further, according to certain embodiments, the outer wall 192 of the handle member 120 and/or the inner slide wall 204 of the adjustable slide 200 can include retention projections that interfere with the ability of the adjustable slide 200 to be displaced away from the first slide position. Thus, when the adjustable slide 200 is to be displaced to the second slide position, a force can be directed upon the adjustable slide 200 that overcomes the force provided by the biasing element and/or retention projections, if any, so that the adjustable slide 200 can be displaced to the second position, as shown in FIG. 16. Alternatively, according to other embodiments, the fastener 216 can be utilized to retain the adjustable slide 200 in the first position. Displacement of the adjustable slide 200 from the first slide position to the second slide position can displace the engagement member 210 to a position that does not interfere with at least the initial engagement of the bone preparation device 102 with the handle member 102, as discussed below.

The handle member 120 can also include a static abutment 218 that can be position to limit the extent the adjustable slide 200 can be axially displaced away from the first slide position and/or control the location of the second slide position. For example, the static abutment 218 can radially extend a distance away from at least a portion of the outer wall 192 of the handle member 120 such that the static abutment 218 interferes with, or otherwise prevents, the passage of the adjustable slide 200 around or past the static abutment 218. According to the illustrated embodiment, the static abutment 218 can have a generally cylindrical shape. However, the static abutment 218 can have a variety of other shapes and sizes. Additionally, according to certain embodiments, the flange portion 208 of the adjustable slide 200 can be sized to engage or otherwise abut against the static abutment 218 in a manner that prevents the passage of the adjustable slide 200 past the static abutment 218. Further, according to certain embodiments, the static abutment 218 can also include a recess 220 that is adapted for connection to an ancillary component of the forming tool 100, such as, for example, an alignment handle.

As shown in at least FIG. 4, according to certain embodiments, at least a portion of the outer wall 192 around a second end 128b of the handle member 120 can include implantation indicia 222 relating to the position and/or orientation of at least the bone preparation device 102 in the bone. For example, according to certain embodiments, the implantation indicia 222 can be a gauge that provides information relating to the depth and/or angle at which the bone preparation device 102 has been inserted into the bone. The implantation indicia 222 can be provided in a number of manners, including, for example, as shown in FIG. 4, as numeric values and/or visual indicators, such as lines or other graphical representations. More specifically, according to certain embodiments, the implantation indicia 222 can be a collection of numeric values that increase in 5 millimeter (mm) increments.

Referencing FIGS. 4 and 15, the second end 128b of the handle member 120 includes a connection member 214 that is adapted to releasably secure the bone preparation device 102 to the handle member 120. A variety of different types of connection members 214 can be utilized, including, for example, a threaded connector that mates a threaded component to the bone preparation device 102. According to the illustrated embodiment, the connection member 214 includes a pair of arms 224a, 224b that extend from the distal end of the outer wall 192. The arms 224a, 224b can each include arm extensions 226a, 226b that each outwardly protrude from a base portion 228a, 228b of the arms 224a, 224b. Additionally, according to certain embodiments, at least a portion of the arms 224a, 224b, such as, for example, the base portion 228a, 228b, can be structured to at least partially deform, bend, or deflect at least when the arm extensions 226a, 226b are being inserted into an aperture 230 of the bone preparation device 102. According to certain embodiments, the aperture 230 of the bone preparation device 102 can include an undercut 232 beneath an upper wall 234 of the bone preparation device 102 that receives the insertion of at least a portion of the arm extensions 226a, 226b. According to such an embodiment, when the arm extensions 226a, 226b are positioned in the aperture 230 of the bone preparation device 102, an upper surface 225 of the arm extensions 226a, 226b can be at least positioned beneath at least a portion of the upper wall 234 of the bone preparation device 102. Such positioning of the arm extensions 226a, 226b beneath the upper wall 234 of the bone preparation device 102 so as to at least assist in retaining a secure attachment or connection between the bone preparation device 102 and the handle member 120. Further, according to the illustrated embodiment, the arms 224a, 224b can be positioned along the second end 154b of the handle member 120 at a location that is positioned away, or radially offset from, the location of the engagement member 210. For example, according to certain embodiments, the engagement member 210 can be positioned at, in opposite directions, about 90 degrees from each of the arms 224a, 224b. However, the engagement member can be located at a variety of other positions relative to the arms 224a, 224b.

Figure 18:
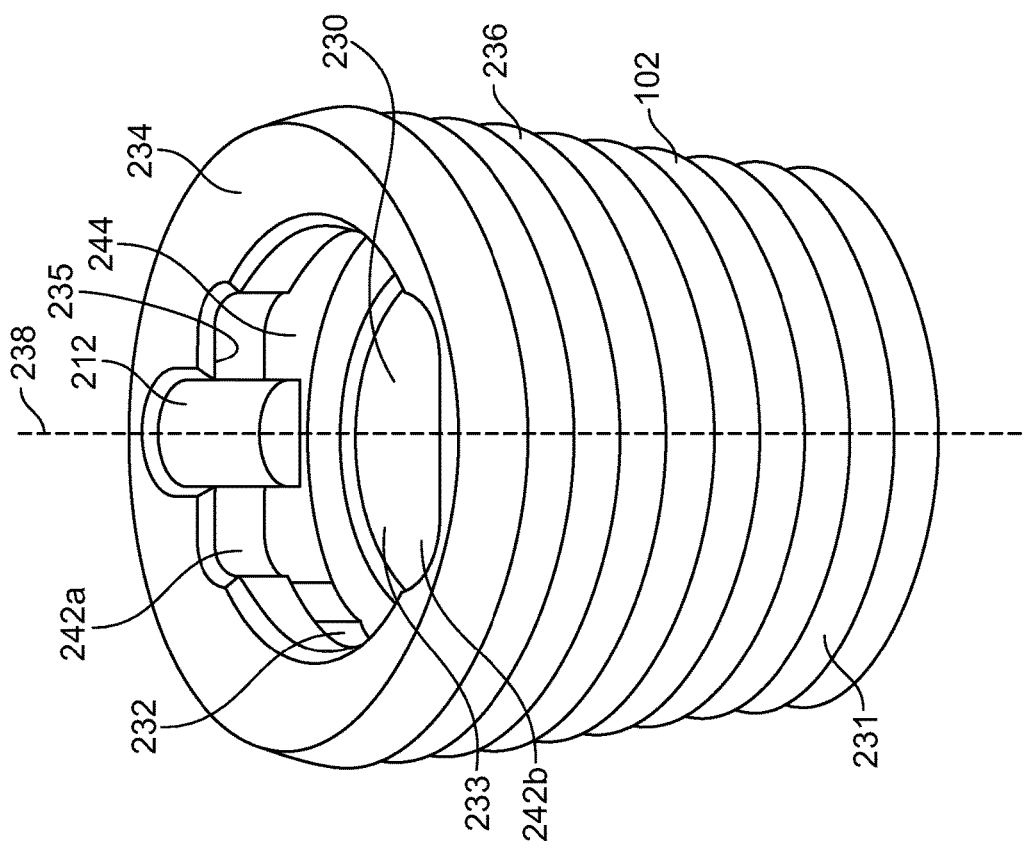
FIG. 18 illustrated a top perspective view of an example of a bone preparation device according to an illustrated embodiment of the present application.

FIG. 18 illustrates a bone preparation device 102 that is structure for operable attachment to the connection member 214 of the forming tool 100 according to an illustrated embodiment of the present application. In the depicted embodiment, the bone preparation device 102 is a broach. However, a variety of other types of bone preparation devices 102 can be used with the forming tool 100, including, for example, a reamer. In the depicted embodiment, the bone preparation device 102 includes a sidewall 231 having an outer surface 236 and an inner surface 244, the outer surface 236 being adapted to facilitate displacement of the bone preparation device 102 into, and/or removal of, the surrounding bone 112. Further, according to certain embodiments, the outer surface 236 of the bone preparation device 102 can symmetrically or asymmetrical extend about a central cutting axis 238. According to the illustrated embodiment, during use, the central cutting axis 238 can be generally positioned in general alignment with the longitudinal handle axis 194 and/or the longitudinal sleeve axis 130. Moreover, in the illustrated embodiment, the longitudinal handle and sleeve axes 294, 130 can be generally aligned with each other to provide a forming axis 240 for the forming tool 100, as shown in FIG. 1.

At least the aperture 230 of the bone preparation device 102 can be configured to facilitate a secure connection between the connection member 214 and the bone preparation device 102. According to the illustrated embodiment, the aperture 230 can be in fluid communication with an opening 233 of the upper wall 234 of the bone preparation device 102, the opening 233 having one or more recesses 242a, 242b that are sized to receive placement of the arm extensions 226a, 226b into at least the aperture 230. The extent to which the arm extensions 226a, 226b can be axially displaced into the aperture 230 can also be limited by an inner surface 244 of the aperture 230 and/or the length of the base portion 228a, 228b of the arms 224a, 224b. Further, according to the illustrated embodiment, a slot 212 can extend outwardly from at least one recess 242a, 242b in the upper wall 234. The slot 212 is configured to receive insertion of at least a portion of the engagement member 210. Further, the engagement of the engagement member 210 with the slot 212 can prevent rotational displacement of at least the handle member 120 relative to the bone preparation device 102.

When the bone preparation device 102 is to be operably connected to the connection member 214, the adjustable slide 200 can be displaced from the first slide position to the second slide position, as shown in FIG. 16. With the adjustable slide 200 in the second slide position, the engagement member 210 can be displaced away from the connection member by a distance that does not interfere with the arm extensions 226a, 226b being inserted into a corresponding recess 242a, 242b. With the arm extension 226a, 226b in the corresponding recess 242a, 242b, the bone preparation device 102 can be rotatably displaced relative to the handle member 120, or vice versa, such that the extension arms 224a, 224b enter into the undercut 232 portion of the aperture 230 beneath an inner wall 235 of the upper wall 234, as shown in FIGS. 17 and 18, and thereby prevents the bone preparation device 102 from being separated from the connection member 214. Further, such rotation can position the engagement member 210 at a location that, when the adjustable slide 200 is returned to the first slide position, at least a portion of the engagement member 210 is received in the slot 212 in the bone preparation device 102 so as to prevent, during use of the forming tool 100, rotational displacement of the bone preparation device 102 relative to the handle member 120.

In the illustrated embodiment, the bone preparation device 102 is a broach. According to such an embodiment, during shaping or forming of the bone 112, an upper end of the forming tool 100 can be impacted by a tool, such as, for example, a mallet, that forces the bone preparation device 102 into the bone 112. The forming tool 100 can continue to be impacted by the tool until the bone preparation device 102 attains a particular depth and/or a particular shape in the bone 112. Further, upon attaining a particular depth or shape in the bone 112, the bone preparation device 102 can be removed from the connection member 214 and replaced with a different sized bone preparation device 102, such as a larger broach, and the process can be repeated until a particular size and/or shape is attained in the bone 112.

While the above example of the forming tool 100 was discussed in terms of use with a bone preparation device 102, a variety of other components can be attached to the forming tool 100 in a similar manner, including, but not limited to, trial components for the implant device. Additionally, according to certain embodiments, the bone preparation device 102 can be indirectly connected to the connection member 214. For example, the connection member 214 can be connected to a first end of an extension or coupling in a similar manner as discussed above with respect to the bone preparation device 102, with the bone preparation device 102 being attached to a second end of the extension or coupling. Additionally, according to certain embodiments, the proximal end 106 of the forming tool 100 is structured for coupling to another instrument that can assist in the formation of the augment opening 114, including, for example, an oscillating saw or drill.

Figure 7A:
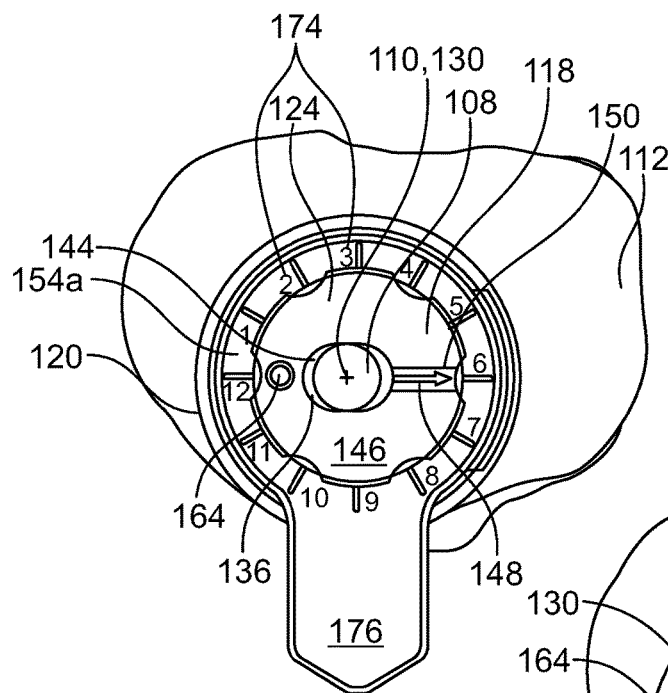
FIGS. 7A-C illustrate top views of an exemplary forming tool in which a guide is positioned at various locations within an elongated guide slot of a sleeve member.
Figure 7B:
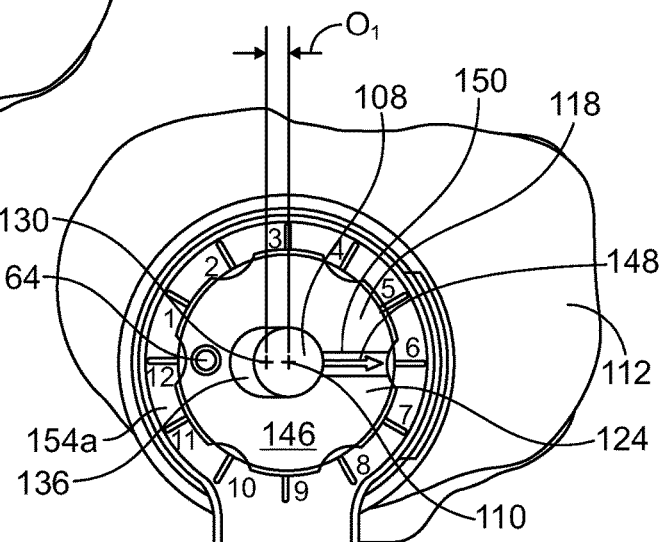
Figure 7C:
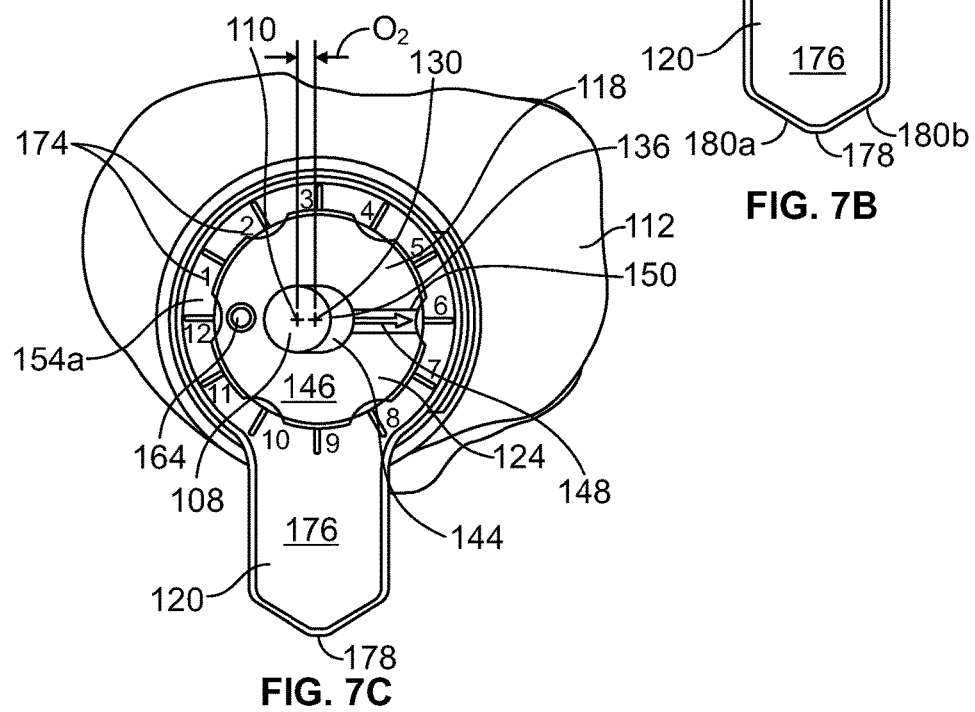
Figures 11, 12:
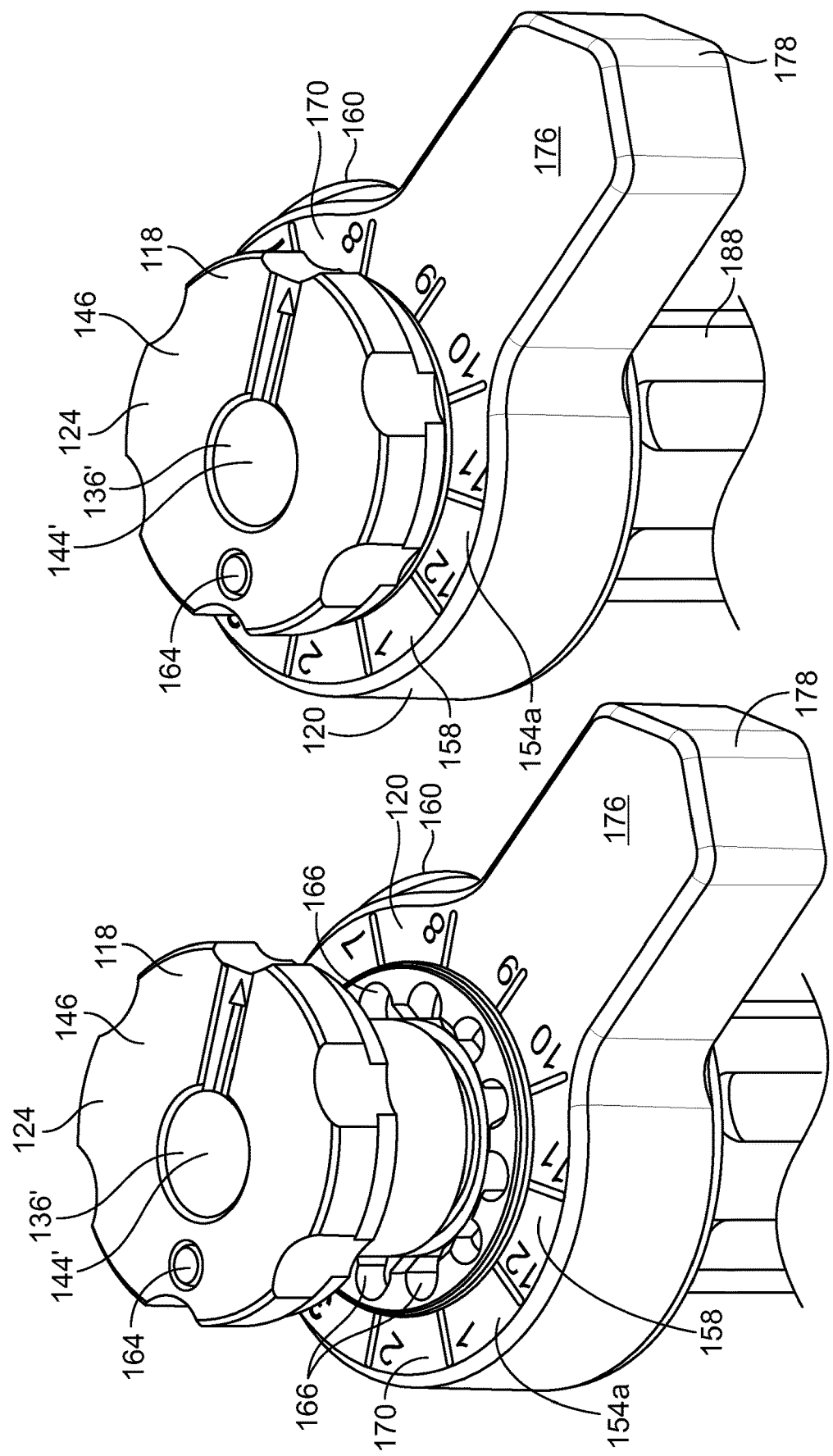
FIG. 11 illustrates a top perspective view of a portion of a forming tool in which a sleeve member having an offset guide slot is being positioned relative to a handle member of the forming tool according to an illustrated embodiment of the present application.
FIG. 12 illustrates a top perspective view of a portion of a forming tool in which a sleeve member having an offset guide slot is secured to a handle member according to an illustrated embodiment of the present application.

Referencing FIGS. 7A-7C, during use, the position of the guide 108, and thus the longitudinal guide axis 110, within the guide slot 136 can provide a reference axis for positioning the central cutting axis 238 and/or the central augment axis 116, which can be at the same location, for forming the augment opening 114 in a bone via use of the forming tool 100. As shown in FIG. 7A, in certain instances, the guide 108 can be positioned within the guide slot 136 so that the longitudinal guide axis 110 is generally positioned along the forming axis 240 of the forming tool 100. Moreover, in such a situation, the longitudinal guide axis 110 can be positioned within the guide slot 136 at a position in which the augment opening 114 formed by use of the forming tool 100 is generally aligned with, or not offset from, the longitudinal guide axis 110. Further, as previously mentioned, the longitudinal guide axis 110 can correspond to, among other axes, the central axis of an intramedullary canal which may, or may not, have previously been shaped for receipt of a stem of an implant device. However, according to other situations, the forming tool 100 can be positioned relative to the guide 108 such that the guide 108 that extends into the guide slot 136 is offset from the forming axis 240. For example, as shown in FIG. 7B, at least the guide slot 136 can be structured so that the guide 108 can be linearly offset from the longitudinal sleeve axis 130, which can be shared by the forming axis 240, such that the forming tool 100 will form an augment opening 114 having a central augment axis 116 that is linearly offset to the left (as indicated by "$O_1$" in FIG. 7B) of at least the longitudinal guide axis 110. Similarly, as shown in FIG. 7C, during other uses, at least the guide slot 136 can be structured so that the guide 108 can be linearly offset from the longitudinal sleeve axis 130, and thus the forming axis 240, such that the forming tool 100 will form an augment opening 114 having a central augment axis that is literally offset to the right (as indicated by "$O_2$" in FIG. 7C) of at least the longitudinal guide axis 110. In the examples provided by FIGS. 7A-7C, the angular position of the longitudinal guide axis 110 relative to at least the longitudinal sleeve axis 130 and/or the forming axis 240 remains the same, as indicated, for example, by the indicator 148 of the selector body 124 remaining at "6" the position. However, as previously discussed, in additional to be linearly offset, as shown in FIGS. 7B and 7C, the angular orientation of the position of at least the longitudinal sleeve axis 130 and/or the forming axis 240 relative to the longitudinal guide axis 110 can be adjusted by adjusting the orientation of the selector body 124, and thus the guide slot 136, relative to at least the selector hub 158.

As previously discussed, FIGS. 8A-8C provide another embodiment of the forming tool 100 in which the guide slots 136' of the sleeve member 118 are pre-set to provide a particular linear offset distance between at least the guide slot axis 138 and the longitudinal axis 130, which in the illustrated embodiment can be positioned along, or shared by, the forming axis 240 and the handle axis 194. Additionally, relative to the settings of the guide slots 136' of the embodiment depicted in FIGS. 7A-7C, the examples provided by FIGS. 8A-8C positioned at linear offset distances of $D_1$, $D_2$, and $D_3$, the guide slot axis 138 are also angularly offset so that, in reference to FIGS. 8A-8C, the guide slot axis 138 are above and to the right of the longitudinal guide axis 110. In the illustrated examples, such angular displacement is attained by setting the indicator 148 of the selector body 124 of the "8" position relative to the selector hub 158, and thereby adjusting the angular location of the guide slot axis 138 relative to the longitudinal sleeve axis 130 and/or the forming axis 240.

Figure 19:
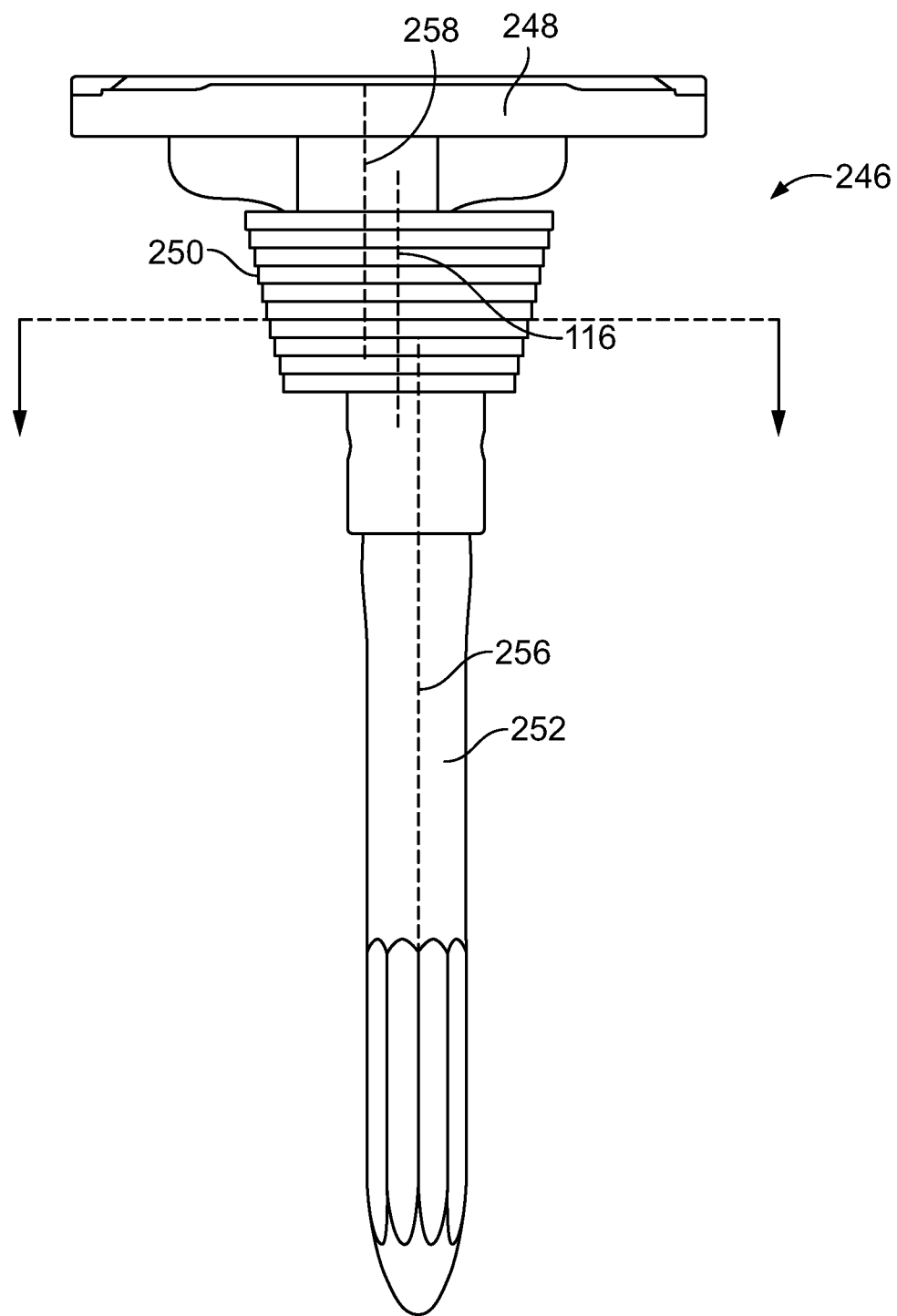
FIG. 19 illustrates a front view of an exemplary tibial implant having a tibial tray, a tibial augment, and a stem.

FIG. 19 illustrates a front view of an exemplary tibial implant 246 having a tibial tray 248, a tibial augment 250, and a stem 252. A variety of different augments can be used for the tibial augment 250, including, for example, a cone or sleeve augment, among other augments. As shown, according to illustrated example, the tibial tray 248 can include a central tray axis 258 that is offset from a central augment axis 116 of the tibial augment 250. Similarly, the stem 252 can extend along a stem axis 256 that is offset from the central augment axis 116 and the tray axis 258, the stem axis 256 and the tray axis 258 being on opposing sides of the central augment axis 116.

Figure 20A:
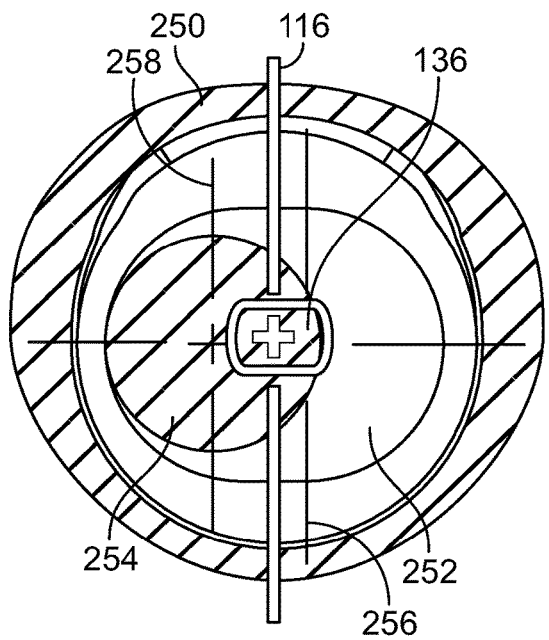
FIGS. 20A-20C illustrate exemplary uses of a forming tool having an elongated guide slot according to certain embodiments of the present application to alter the location of the central augment axis, and thus the location of the tibial augment in a bone, relative to at least a stem and/or a tibial tray of a tibial implant.
Figure 20B:
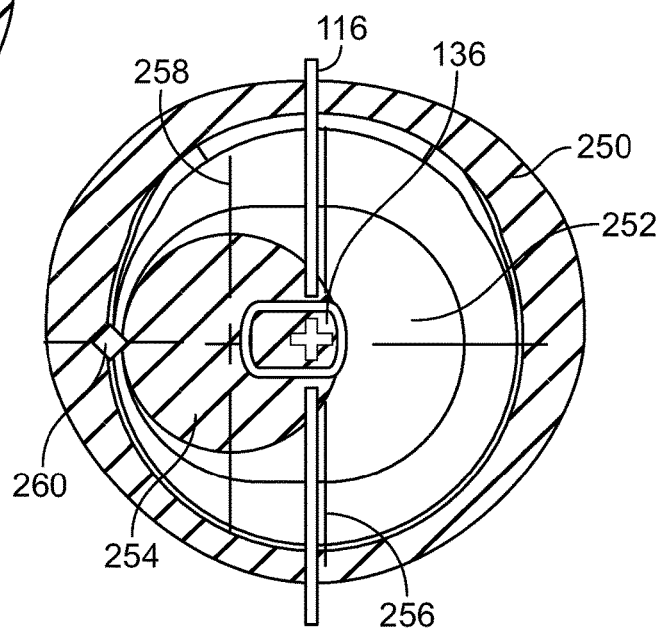
Figure 20C:
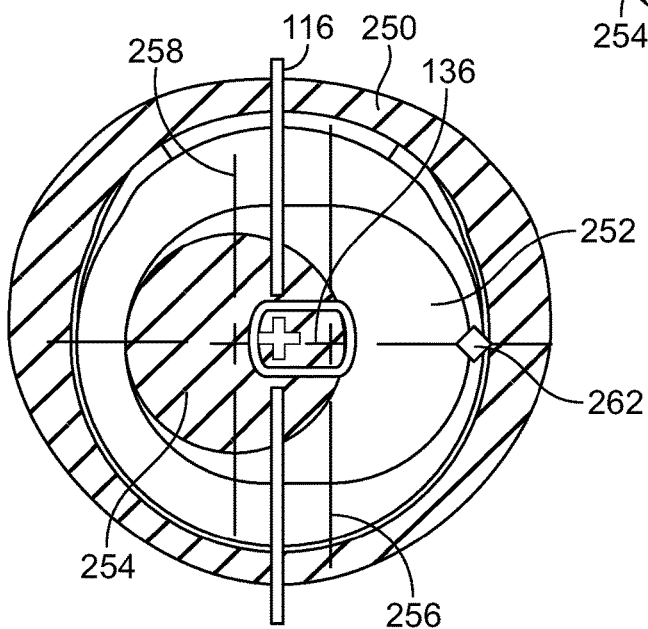

FIGS. 20A-20C illustrate examples of use of a forming tool 100 having an elongated guide slot 136 similar to that depicted in FIGS. 5 and 7A-7C to alter the location of the central augment axis 116, and thus the location of the tibial augment 250, in the bone 112, relative to at least the stem 252 and/or the tibial tray 248. In the illustrated embodiment, adjustments in the positioning of the forming tool 100 that are provided by the size of the guide slot 136, such as the linear length of the guide slot 136 (as indicated by "L" in FIG. 9), can facilitate the location of the formed central augment axis 116 relative to either, or both, of the longitudinal stem axis 256 and tray axis 258. Moreover, such adjustment of the location of the central augment axis 116 can impact the location of the associated tibial augment 250 and the stem 252 and/or tibial tray 248. For example, as shown in FIG. 20A, the forming tool 100 can be oriented to position the central augment axis 116 at a generally central location between the longitudinal stem axis 256 and tray axis 258. However, the elongated configuration of the guide slot 136 can provide the ability to linearly displace the position of the forming tool 100 in a first direction so as to decrease the distance between the central augment axis 116 and the stem axis 256, or increase the distance between the central augment axis 116 and the tray axis 258, as shown, for example, in FIG. 20B. Further, according to certain embodiments, the guide slot 136 can have a length that allows the central augment axis 116 to be positioned at a location where a portion of the tibial tray 248, such as, for example, a tray stem 254, can contact the tibial augment 250 at a first contact location 260. Similarly, the elongated configuration of the guide slot 136 can provide the ability to linearly displace the position of the forming tool 100 in a second direction so as to decrease the distance between the central augment axis 116 and tibial tray axis 258, or increase the distance between the central augment axis 116 and the stem axis 256, as shown, for example, in FIG. 20C. Further, according to certain embodiments, the guide slot 136 can have a length that allows the central augment axis 116 to be portioned at a location where a portion of the stem 252 can contact the tibial augment 250 at a second contact location 262.

Figure 21A:
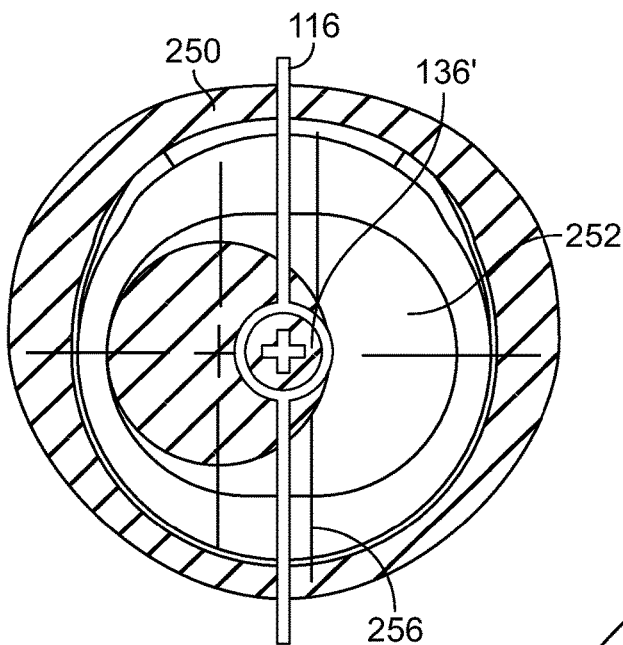
FIGS. 21A-21C illustrate exemplary uses of a forming tool having an offset guide slot according to certain embodiments of the present application to alter the location of the central augment axis, and thus the location of the tibial augment in a bone, relative to at least a stem and/or a tibial tray of a tibial implant.
Figure 21B:
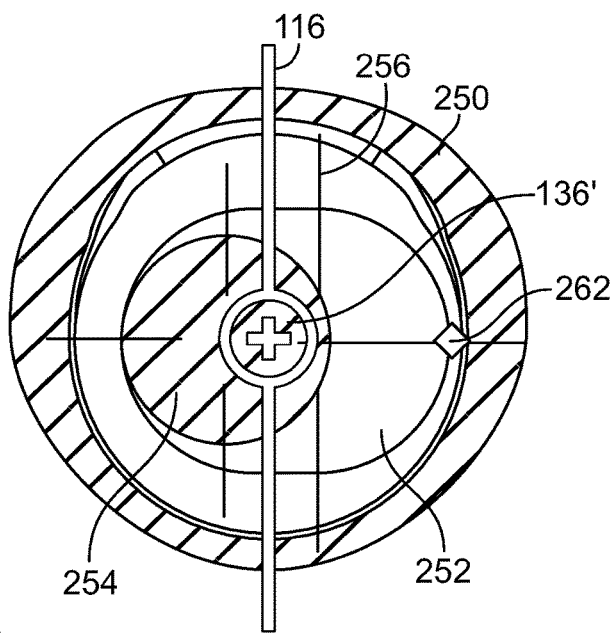
Figure 21C:
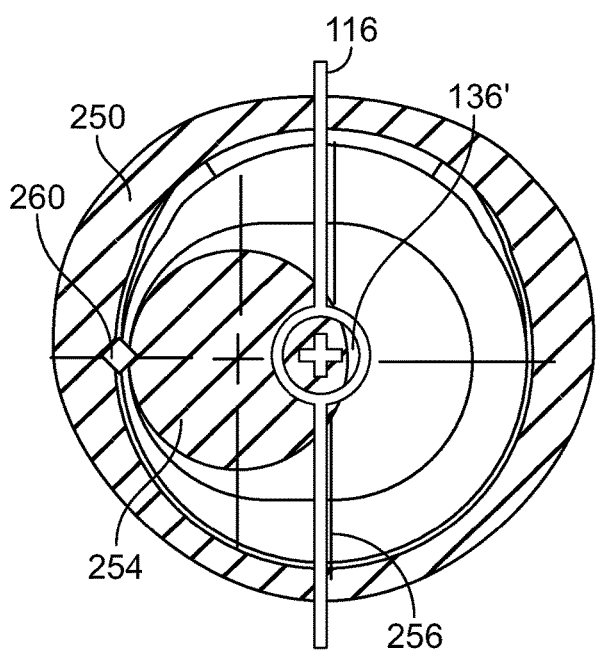

FIGS. 21A-C also illustrate use of the forming tool 100 to adjust the location of the central augment axis 116 relative to the tray axis 258 and stem axis 256, but via use three sleeve members that are similar to the sleeve members 118 and guide slots 136' shown in FIGS. 6 and 8A-8C. Moreover, the linear offset distance provided by each of the guide slots 136' illustrated in FIGS. 21A-C differ and/or the angular orientation is altered so as to vary the linear distance between the central augment axis 116 and the stem axis 256 and tibial tray axis. For example, FIG. 21A illustrates use of a sleeve member 118 having a guide slot 136' that has a linear offset distance that is less than that shown for the guide slot 136' associated with FIG. 21B. Accordingly, compared to the guide slot 136' used in FIG. 21A, the guide slot 136' associated with FIG. 21B has a linear offset distance such that, when used with the same angular orientation, brings the central augment axis 116 into closer proximity to the tibial tray axis 258, and increases the distance between the central augment axis 116 and the stem axis 256. Similar to FIG. 20C, the offset provided by the positioning of the guide slot 136' can allow the central augment axis 116 to be positioned at a location where a portion of the stem 252 can contact the tibial augment 250 at a second contact location 262. FIG. 21C illustrates use of a sleeve member 118 having a guide slot 136' that provides the same or similar offset as provided by the guide slot 136' shown in FIG. 21B, but with the angular position of the guide slot rotated approximately 180 degrees. Moreover, referencing FIGS. 8A-8C, the alignment of the central augment axis 116 relative to the stem axis 256 and/or tibial tray axis 258 shown in FIG. 21B may have been attained by aligning the indicator 148 of the sleeve member 118 at the "6" position, while of the alignment central augment axis 116 shown in FIG. 21C may have been attained by aligning the indicator 148 of the same sleeve member 118 in the "12" position. Thus, in this example, by altering the angular position of guide slot, compared to FIGS. 21A and 21B, the central augment axis 116 is extended further from the tibial tray axis 258, and the distance between the central augment axis 116 and the stem axis 256 is decreased. Further the guide slot 136' shown in FIG. 21C can, similar to FIG. 20B, provide a linear offset distance that allows the central augment axis 116 to be positioned at a location where a portion of the tibial tray 248, such as, for example, a tray stem 254, can contact the tibial augment 250 at the first contact location 260.

While the invention has been described in connection with what is presently considered to be the most practical and preferred embodiment, it is to be understood that the invention is not to be limited to the disclosed embodiment (s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described can be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. An apparatus for use with a bone preparation device, the apparatus comprising:
a sleeve member having a guide slot sized to receive axial passage of at least a portion of a guide, the guide slot sized to accommodate linear displacement of the sleeve member about the guide in one or more directions perpendicular to a longitudinal guide axis of the guide;
a handle member having an inner area sized to receive insertion of at least a portion of the sleeve member, the handle member having a connection member structured to be coupled to the bone preparation device; and
a retention member adapted to selectively secure the sleeve member to the handle member at a selected one of a plurality of rotational positions, each of the plurality of rotational positions adjusting an angular position of at least the sleeve member relative to the handle member.

2. The apparatus of claim 1, wherein the guide slot extends about a central guide slot axis that is offset from a longitudinal sleeve axis of the sleeve member.

3. The apparatus of claim 2, wherein the longitudinal sleeve axis is generally aligned with a longitudinal handle axis of the handle member.

4. The apparatus of claim 1, wherein the retention member includes a mating engagement between one or more projections of either the handle member and the sleeve member with one or more recesses of the other of the handle member and the sleeve member.

5. The apparatus of claim 4, wherein the one or more projections comprises a pin that extends from the sleeve member, and wherein the one more recesses comprises a plurality or recesses in the handle member, each of the plurality of recesses structured to receive selective insertion of at least a portion of the pin.

6. The apparatus of claim 1, wherein the handle member further includes a selector hub having a plurality of indexes indicative of one or more of the plurality or rotational positions.

7. The apparatus of claim 6, wherein the sleeve member includes an indicator that, when the sleeve member is selectively secured to the handle member by the retention member, generally aligns with at least one of the plurality of indicia to indicate the selected one of the plurality rotational positions.

8. The apparatus of claim 1, wherein the connection member comprises a first arm and a second arm, the first and second arms extending from a distal end of the handle member, the first and second arms adapted to securely engage the bone preparation device.

9. The apparatus of claim 8, wherein the connection member includes an adjustable slide that is coupled to the first and second arms, the first and second arms adapted to be axially displaced by axial displacement of the adjustable slide along at least a portion of the handle member.

10. The apparatus of claim 9, wherein the adjustable slide is adapted for rotational displacement about at least a portion of the handle member, and wherein the first and second arms each include a base portion and an arm extension, the arm extension being generally perpendicular to the base portion and structured to be received in an undercut of the bone preparation device.

11. An apparatus for use with a bone preparation device, the apparatus comprising:
a sleeve member having a guide slot sized to receive axial passage of at least a portion of a guide, the guide slot having a central guide slot axis that is offset from a longitudinal sleeve axis of the sleeve member;
a handle member having an inner area sized to receive removable insertion of at least a portion of the sleeve member, the handle member having a connection member structured to be coupled to the bone preparation device; and
a retention member adapted to selectively secure the sleeve member to the handle member at a selected one of a plurality of rotational positions, each of the plurality of rotational positions adjusting an angular position of at least the guide slot relative to a longitudinal handle axis of the handle member.

12. The apparatus of claim 11, wherein the retention member includes a mating engagement between one or more projections of either the handle member and the sleeve member with one or more recesses of the other of the handle member and the sleeve member.

13. The apparatus of claim 12, wherein the one or more projections comprises a pin that extends from the sleeve member, and wherein the one more recesses comprises a plurality of recesses in the handle member, each of the plurality of recesses structured to receive selective insertion of at least a portion of the pin.

14. The apparatus of claim 11, wherein the handle member further includes a selector hub having a plurality of indicia indicative of one or more of the plurality or rotational positions.

15. The apparatus of claim 14, wherein the sleeve member includes an indicator that, when the sleeve member is selectively secured to the handle member by the retention member, generally aligns with at least one of the plurality of indicia to indicate the selected one of the plurality rotational positions.

16. The apparatus of claim 11, wherein the connection member comprises a first arm and a second arm, the first and second arms extending from a distal end of the handle member, the first and second arms adapted to securely engage the bone preparation device.

17. The apparatus of claim 16, wherein the connection member includes an adjustable slide that is coupled to the first and second arms, the first and second arms adapted to be axially displaced by axial displacement of the adjustable slide along at least a portion of the handle member.

18. The apparatus of claim 17, wherein the adjustable slide is adapted for rotational displacement about at least a portion of the handle member, and wherein the first and second arms each include a base portion and an arm extension, the arm extension being generally perpendicular to the base portion and structured to be received in an undercut of the bone preparation device.

* * * * *